US010471249B2

(12) United States Patent
Heikenfeld et al.

(10) Patent No.: US 10,471,249 B2
(45) Date of Patent: Nov. 12, 2019

(54) ENHANCED ANALYTE ACCESS THROUGH EPITHELIAL TISSUE

(71) Applicants: University Of Cincinnati, Cincinnati, OH (US); Eccrine Systems, Inc., West Chester, OH (US)

(72) Inventors: Jason Charles Heikenfeld, Cincinnati, OH (US); Andrew Jajack, Cincinnati, OH (US); Michael Charles Brothers, Covington, KY (US)

(73) Assignee: University of Cincinnati, Cincinnati, OH (US)

( * ) Notice: Subject to any disclaimer, the term of this patent is extended or adjusted under 35 U.S.C. 154(b) by 125 days.

(21) Appl. No.: 15/617,649

(22) Filed: Jun. 8, 2017

(65) Prior Publication Data

US 2017/0354808 A1 Dec. 14, 2017

Related U.S. Application Data

(60) Provisional application No. 62/347,281, filed on Jun. 8, 2016.

(51) Int. Cl.
*A61N 1/30* (2006.01)
*A61N 1/04* (2006.01)
(Continued)

(52) U.S. Cl.
CPC ........ *A61N 1/0444* (2013.01); *A61B 5/14517* (2013.01); *A61B 5/4839* (2013.01);
(Continued)

(58) Field of Classification Search
CPC ...... A61M 2037/0007; A61M 2202/07; A61M 2202/08; A61M 2230/20; A61M 37/00;
(Continued)

(56) References Cited

U.S. PATENT DOCUMENTS

| 4,190,060 A | 2/1980 | Greenleaf et al. |
| 4,542,751 A | 9/1985 | Webster et al. |

(Continued)

FOREIGN PATENT DOCUMENTS

| CA | 2869469 A1 | 10/2013 |
| CN | 101489470 A | 7/2009 |

(Continued)

OTHER PUBLICATIONS

International Searching Authority, Search Report and Written Opinion issued in related International Application No. PCT/US2017/013453 dated May 18, 2017, 14 pages.

(Continued)

*Primary Examiner* — Rebecca E Eisenberg
(74) *Attorney, Agent, or Firm* — Wood Herron & Evans LLP

(57) ABSTRACT

A device for increasing a concentration of at least one analyte in an advective flow of biofluid includes an agent for enhancing a paracellular permeability of an epithelial tissue; and an iontophoresis electrode and a counter electrode, which are adapted to increase the concentration of said analyte in the advective flow of the biofluid. A method of sensing an analyte in a biofluid includes increasing a paracellular permeability of an epithelial tissue layer; and inducing electro-osmotic flow by reverse iontophoresis to increase a concentration of said analyte in an advective flow of the biofluid, wherein said advective flow is driven by at least one of saliva generation, sweat generation, or reverse iontophoresis.

15 Claims, 5 Drawing Sheets

(51) Int. Cl.
  *A61N 1/32* (2006.01)
  *A61B 5/145* (2006.01)
  *A61B 5/00* (2006.01)
  *A61B 10/00* (2006.01)
  *A61N 1/05* (2006.01)
  *A61M 37/00* (2006.01)

(52) U.S. Cl.
  CPC ........ *A61B 10/0064* (2013.01); *A61N 1/0432* (2013.01); *A61N 1/0448* (2013.01); *A61N 1/0548* (2013.01); *A61N 1/325* (2013.01); *A61M 2037/0007* (2013.01); *A61M 2202/07* (2013.01); *A61M 2202/08* (2013.01); *A61M 2230/20* (2013.01)

(58) Field of Classification Search
  CPC .. A61N 1/0432; A61N 1/0444; A61N 1/0448; A61N 1/0548; A61N 1/325
  See application file for complete search history.

(56) References Cited

U.S. PATENT DOCUMENTS

| | | | |
|---|---|---|---|
| 4,756,314 A | 7/1988 | Eckenhoff et al. | |
| 4,820,263 A | 4/1989 | Spevak et al. | |
| 5,036,861 A | 8/1991 | Sembrowich et al. | |
| 5,050,604 A | 9/1991 | Reshef et al. | |
| 5,140,985 A | 8/1992 | Schroeder et al. | |
| 5,246,003 A | 9/1993 | DeLonzor | |
| 5,438,984 A | 8/1995 | Schoendorfer | |
| 5,556,789 A | 9/1996 | Goerlach-Graw et al. | |
| 5,814,599 A | 9/1998 | Mitragotri et al. | |
| 5,944,662 A | 8/1999 | Schoendorfer | |
| 6,198,953 B1 | 3/2001 | Webster et al. | |
| 6,256,533 B1 | 7/2001 | Yuzhakov et al. | |
| 6,269,265 B1 | 7/2001 | Anderson | |
| 6,299,578 B1 | 10/2001 | Kurnik et al. | |
| 6,592,529 B2 | 7/2003 | Marett | |
| 6,666,821 B2 | 12/2003 | Keimel | |
| 7,190,986 B1 | 3/2007 | Hannula et al. | |
| 7,219,534 B2 | 5/2007 | Campbell | |
| 7,378,054 B2 | 5/2008 | Karmali | |
| 7,383,072 B2 | 6/2008 | Edmonson et al. | |
| 7,384,396 B2 | 6/2008 | Samuels et al. | |
| 7,749,445 B2 | 7/2010 | Masters | |
| 7,813,780 B2 | 10/2010 | Shah et al. | |
| 7,842,234 B2 | 11/2010 | Lauks et al. | |
| 7,959,791 B2 | 6/2011 | Kjaer et al. | |
| 8,125,539 B2 | 2/2012 | Takashima | |
| 8,128,889 B2 | 3/2012 | Fujimoto et al. | |
| 8,252,248 B2 | 8/2012 | Kramer | |
| 8,391,946 B2 | 3/2013 | Sugenoya et al. | |
| 8,565,850 B2 | 10/2013 | Martinsen et al. | |
| 8,593,287 B2 | 11/2013 | Hayter et al. | |
| 8,617,067 B2 | 12/2013 | Jain et al. | |
| 9,133,024 B2 | 9/2015 | Phan et al. | |
| 2002/0091312 A1 | 7/2002 | Berner et al. | |
| 2003/0135100 A1 | 7/2003 | Kim et al. | |
| 2003/0191376 A1 | 10/2003 | Samuels et al. | |
| 2003/0201194 A1 | 10/2003 | Heller et al. | |
| 2004/0249310 A1 | 12/2004 | Shartle et al. | |
| 2004/0267189 A1 | 12/2004 | Mavor et al. | |
| 2005/0069925 A1 | 3/2005 | Ford et al. | |
| 2005/0106713 A1 | 5/2005 | Phan et al. | |
| 2005/0177035 A1 | 8/2005 | Botvinick et al. | |
| 2005/0192528 A1 | 9/2005 | Tapper | |
| 2005/0197554 A1 | 9/2005 | Polcha | |
| 2006/0004271 A1 | 1/2006 | Peyser et al. | |
| 2006/0062852 A1 | 3/2006 | Holmes | |
| 2006/0127964 A1 | 6/2006 | Ford et al. | |
| 2006/0253011 A1 | 11/2006 | Edmonson et al. | |
| 2006/0254341 A1 | 11/2006 | Campbell | |
| 2007/0027383 A1 | 2/2007 | Peyser et al. | |
| 2007/0032731 A1 | 2/2007 | Lovejoy et al. | |
| 2007/0179371 A1 | 8/2007 | Peyser et al. | |
| 2008/0015494 A1 | 1/2008 | Santini et al. | |
| 2008/0045816 A1 | 2/2008 | Jang et al. | |
| 2008/0114282 A1* | 5/2008 | Carter ............... | A61N 1/044 604/20 |
| 2008/0154179 A1 | 6/2008 | Cantor et al. | |
| 2008/0286349 A1 | 11/2008 | Nomoto et al. | |
| 2008/0306362 A1 | 12/2008 | Davis | |
| 2009/0076345 A1 | 3/2009 | Manicka et al. | |
| 2009/0204008 A1 | 8/2009 | Beilin | |
| 2009/0270704 A1 | 10/2009 | Peyser et al. | |
| 2010/0044224 A1 | 2/2010 | Kataky | |
| 2010/0063372 A1 | 3/2010 | Potts et al. | |
| 2010/0130843 A1 | 5/2010 | Caceres Galvez et al. | |
| 2010/0132485 A1 | 6/2010 | Erez et al. | |
| 2010/0198521 A1 | 8/2010 | Haick | |
| 2011/0079521 A1 | 4/2011 | Revol-Cavalier | |
| 2011/0118656 A1 | 5/2011 | Eckhoff et al. | |
| 2011/0178380 A1 | 7/2011 | Chowdhury | |
| 2011/0196283 A1 | 8/2011 | Imran et al. | |
| 2011/0208458 A1 | 8/2011 | Pinter et al. | |
| 2011/0275918 A1 | 11/2011 | Yamashita et al. | |
| 2012/0004570 A1 | 1/2012 | Shimizu et al. | |
| 2012/0028283 A1 | 2/2012 | Hoss et al. | |
| 2012/0123220 A1 | 5/2012 | Iyer et al. | |
| 2012/0165626 A1 | 6/2012 | Irina et al. | |
| 2012/0209226 A1 | 8/2012 | Simmons et al. | |
| 2012/0229661 A1 | 9/2012 | Sekiguchi et al. | |
| 2012/0277697 A1 | 11/2012 | Haghgooie et al. | |
| 2012/0285829 A1 | 11/2012 | Mount et al. | |
| 2012/0317430 A1 | 12/2012 | Rahman et al. | |
| 2012/0323097 A9 | 12/2012 | Chowdhury | |
| 2013/0006079 A1 | 1/2013 | Feldman et al. | |
| 2013/0010108 A1 | 1/2013 | Hashizume et al. | |
| 2013/0013028 A1 | 1/2013 | Kriksunov et al. | |
| 2013/0053668 A1 | 2/2013 | Lin | |
| 2013/0079605 A1 | 3/2013 | Bandaru et al. | |
| 2013/0099937 A1 | 4/2013 | Azimi | |
| 2013/0108667 A1 | 5/2013 | Soikum et al. | |
| 2013/0123595 A1 | 5/2013 | Currie et al. | |
| 2013/0183399 A1 | 7/2013 | Blow et al. | |
| 2013/0306491 A1 | 11/2013 | Briman et al. | |
| 2013/0317333 A1 | 11/2013 | Yang et al. | |
| 2014/0012114 A1 | 1/2014 | Zevenbergen et al. | |
| 2014/0025000 A1 | 1/2014 | Currie et al. | |
| 2014/0206977 A1 | 7/2014 | Bahney et al. | |
| 2014/0275862 A1 | 9/2014 | Kennedy | |
| 2014/0276220 A1 | 9/2014 | Briscoe et al. | |
| 2014/0343371 A1 | 11/2014 | Sowers, II et al. | |
| 2015/0057515 A1 | 2/2015 | Hagen et al. | |
| 2015/0112164 A1 | 4/2015 | Heikenfeld et al. | |
| 2015/0112165 A1 | 4/2015 | Heikenfeld | |
| 2016/0058354 A1 | 3/2016 | Phan et al. | |
| 2016/0066828 A1 | 3/2016 | Phan et al. | |
| 2016/0157768 A1 | 6/2016 | Braig et al. | |

FOREIGN PATENT DOCUMENTS

| | | |
|---|---|---|
| EP | 0282349 A2 | 9/1988 |
| EP | 0453283 A1 | 10/1991 |
| EP | 0634215 A1 | 1/1995 |
| EP | 1500937 A1 | 1/2005 |
| EP | 1637889 A1 | 3/2006 |
| EP | 2551784 A1 | 1/2013 |
| JP | H07-77525 A | 3/1995 |
| JP | H08-504513 A | 5/1996 |
| JP | 2007503958 A | 3/2007 |
| JP | 2007532260 A | 11/2007 |
| JP | 2008505330 A | 2/2008 |
| JP | 200963597 A | 3/2009 |
| JP | 2009118420 A | 5/2009 |
| WO | 9011519 A1 | 10/1990 |
| WO | 9414062 A1 | 6/1994 |
| WO | 0014535 A1 | 3/2000 |
| WO | 01/88525 A1 | 11/2001 |
| WO | 2006133101 A2 | 12/2006 |
| WO | 2007097754 A1 | 8/2007 |
| WO | 2007146047 A1 | 12/2007 |
| WO | 2008083687 A1 | 7/2008 |
| WO | 2008095940 A1 | 8/2008 |

(56) References Cited

FOREIGN PATENT DOCUMENTS

| WO | 2009004001 A1 | 1/2009 |
|---|---|---|
| WO | 2009052321 A2 | 4/2009 |
| WO | 2010/017578 A1 | 2/2010 |
| WO | 2011117952 A1 | 9/2011 |
| WO | 2013152087 A2 | 10/2013 |
| WO | 2013181436 A1 | 12/2013 |
| WO | 2014001577 A1 | 1/2014 |
| WO | 2014025430 A2 | 2/2014 |
| WO | 2015184072 A1 | 12/2015 |
| WO | 2015184097 A2 | 12/2015 |
| WO | 2016049019 A1 | 3/2016 |
| WO | 2016061362 A2 | 4/2016 |
| WO | 2016090189 A1 | 6/2016 |
| WO | 2016130905 A1 | 8/2016 |
| WO | 2016138087 A1 | 9/2016 |
| WO | 2017019602 A1 | 2/2017 |
| WO | 2017070640 A1 | 4/2017 |

OTHER PUBLICATIONS

International Searching Authority, Search Report and Written Opinion issued in related International Application No. PCT/US2017/039421 dated Sep. 6, 2017, 10 pages.
International Searching Authority, Search Report and Written Opinion issued in related International Application No. PCT/US2017/040588 dated Sep. 25, 2017, 11 pages.
European Patent Office, Supplemental European Search Report issued in European Application No. 15799514.3-1657 dated Dec. 7, 2017, 8 pages.
European Patent Office, Supplemental European Search Report issued in European Application No. 15799317.1-1657 dated Dec. 21, 2017, 9 pages.
European Patent Office, Partial European Search Report issued in European Application No. 15800043.0-115 dated Jan. 8, 2018, 13 pages.
International Searching Authority, Search Report and Written Opinion issued in International Application No. PCT/US2017/047574 dated Nov. 16, 2017, 14 pages.
International Searching Authority, Search Report and Written Opinion issued in International Application No. PCT/US2017/052651 dated Dec. 12, 2017, 14 pages.
Pike, Douglas J., et al., "Flow Cell Design for Effective Biosensing," Sensors, ISSN 1424-8220, Dec. 2012, vol. 13, pp. 58-70, www.mdpi.com/journal/sensors, 13 pages.
Sonner, Z., et al., "The microfluidics of the eccrine sweat gland, including biomarker partitioning, transport, and biosensing implications," Biomicrofluidics, vol. 9, pp. 031301-1-031301-19, CrossMark, 19 pages.
European Patent Office, Official Communication for EP Application No. 13 718 933.8-1101 dated Feb. 14, 2018 (5 pages).
European Patent Office, Extended European Search Report issued in European Application No. 15819306.0-1115 dated Feb. 9, 2018 (9 pages).
International Searching Authority, Search Report and Written Opinion issued in International Application No. PCT/US2017/067495 dated Mar. 1, 2018, 10 pages.
International Searching Authority/US, International Search Report and Written Opinion issued in corresponding PCT Application No. PCT/US2016/059392, dated Feb. 15, 2017 (12 pages).
European Patent Office, Extended Search Report issued in European Application No. 15844313.5 dated Mar. 15, 2018, 15 pages.
De Jong, J. et al., "Membranes and microfluidics: a review," Lab Chip, 2006, 6, 1125-1139 (15 pages).
Yamazaki, T. et al., "Smart Integrated Sensor for Multiple Detections of Glucose and L-Lactate Using On-Chip Electrochemical System," Journal of Sensors, vol. 2011, Article ID 190284, doi:10.1155/2011/190284, Accepted Apr. 26, 2011, 7 pages.
European Patent Office, Extended Search Report issued for European Application No. 15800043.0-1115 dated Apr. 16, 2018, 11 pages.

Australian Patent Office, Patent Examination Report No. 1 issued in Australian Application No. 2013243541 dated Nov. 25, 2016, 4 pages.
Australian Patent Office, Notice of Acceptance for Patent Application issued in Australian Application No. 2013243541 dated Mar. 23, 2017 (3 pages).
Chinese Patent Office, First Office Action issued in Chinese Application No. 201380028053.8 dated Dec. 21, 2015, 4 pages.
Chinese Patent Office, Second Office Action issued in Chinese Application No. 201380028053.8 dated Sep. 20, 2016, 8 pages (including English language translation).
Chinese Patent Office, Third Office Action issued in Chinese Application No. 201380028053.8 dated Mar. 20, 2017, 17 pages (including English language translation).
European Patent Office, Written Opinion of the International Searching Authority / International Preliminary Report on Patentability dated Oct. 16, 2014 (14 pages).
European Patent Office, Partial European Search Report issued in European Application No. 16203346.8-1657 dated Mar. 24, 2017, 7 pages.
Fu et al., "Controlled Reagent Transport in Disposable 2D Paper Networks", The Royal Society of Chemistry 2010, Lab Chip, 2010, 10, 918-920.
International Bureau, Notification Concerning Transmittal of Copy of International Preliminary Report on Patentability issued in International Application No. PCT/US13/35092 dated Oct. 7, 2014, 14 pages.
International Searching Authority, Invitation to Pay Additional Fees and, Where Applicable, Protest Fee, and Communication Relating to the Results of the Partial International Search, issued in International Application No. PCT/US13/35092 dated Aug. 26, 2013, 9 pages.
International Searching Authority, Invitation to Pay Additional Search Fees and, Where Applicable, Protest Fee, and Communication Relating to the Results of the Partial International Search, issued in International Application No. PCT/US2014/061083 dated Dec. 15, 2014, 6 pages.
International Searching Authority, Invitation to Pay Additional Search Fees and, Where Applicable, Protest Fee, and Communication Relating to the Results of the Partial International Search, issued in International Application No. PCT/US2015/032843 dated Aug. 18, 2015, 2 pages.
International Searching Authority, Invitation to Pay Additional Search Fees and, Where Applicable, Protest Fee, and Communication Relating to the Results of the Partial International Search, issued in International Application No. PCT/US2015/032866 dated Aug. 31, 2015, 2 pages.
International Searching Authority, Invitation to Pay Additional Search Fees and, Where Applicable, Protest Fee, and Communication Relating to the Results of the Partial International Search, issued in International Application No. PCT/US2015/032893 dated Aug. 31, 2015, 2 pages.
International Searching Authority, Invitation to Pay Additional Search Fees and, Where Applicable, Protest Fee, and Communication Relating to the Results of the Partial International Search, issued in International Application No. PCT/US2015/040113 dated Dec. 1, 2015, 2 pages.
International Searching Authority, Search Report and Written Opinion issued in International Application No. PCT/US2014/061098 dated Dec. 19, 2014, 13 pages.
International Searching Authority, Search Report and Written Opinion issued in International Application No. PCT/US2014/061083 dated Mar. 31, 2015, 18 pages.
International Searching Authority, Search Report and Written Opinion issued in International Application No. PCT/US2015/032830 dated Aug. 14, 2015, 9 pages.
International Searching Authority, Search Report and Written Opinion issued in International Application No. PCT/US2015/032843 dated Oct. 26, 2015, 11 pages.
International Searching Authority, Search Report and Written Opinion issued in International Application No. PCT/US2015/032893 dated Nov. 13, 2015, 14 pages.

(56) References Cited

OTHER PUBLICATIONS

International Searching Authority, Search Report and Written Opinion issued in International Application No. PCT/US2015/032866 dated Nov. 19, 2015, 12 pages.

International Searching Authority, Search Report and Written Opinion issued in International Application No. PCT/US2015/051439 dated Dec. 28, 2015, 7 pages.

International Searching Authority, Search Report and Written Opinion issued in International Application No. PCT/US2015/040113 dated Feb. 4, 2016, 13 pages.

International Searching Authority, Search Report and Written Opinion issued in International Application No. PCT/US16/18635 dated May 6, 2016, 12 pages.

International Searching Authority, Search Report and Written Opinion issued in International Application No. PCT/US16/17726 dated May 12, 2016, 9 pages.

International Searching Authority, Search Report and Written Opinion issued in International Application No. PCT/US16/50928 dated Sep. 9, 2016, 8 pages.

International Searching Authority, Search Report and Written Opinion issued in International Application No. PCT/US16/43862 dated Oct. 19, 2016, 14 pages.

International Searching Authority, Search Report and Written Opinion issued in International Application No. PCT/US16/59392 dated Oct. 28, 2016, 13 pages.

Japanese Patent Office, Office Action issued in Japanese Application No. 2015-504702 dated Jan. 20, 2017, 7 pages (including English language translation).

Saini, Vipin, et al., "Non Invasive Therapeutic Drug Monitoring of Propranolol Hydrochloride by Reverse Iontophoresis," International Research Journal of Pharmacy, 2012, vol. 3(4), pp. 395-399 (6 pages).

Stoppa, Matteo, et al., "Wearable Electronics and Smart Tectiles: A Critical Review," Sensors, 2014, pp. 11957-11992, vol. 14 (36 pages).

* cited by examiner

ENHANCED ANALYTE ACCESS THROUGH EPITHELIAL TISSUE

BACKGROUND OF THE INVENTION

The ways in which we approach wellness are changing—reactionary methods are being replaced with preventative measures, medicine is becoming personalized, and consumers are seeking more ways to monitor their day-to-day health. It is no surprise that the market for wearable biosensors has taken off in recent years. However, the sensors of today are limited in data that they collect. These devices rely on decades-old optical- and electrical-based sensors and are largely limited to measuring pulse and tracking movement. While useful for some applications like fitness tracking, this level of detail is simply inadequate to meet the goal of providing truly useful and actionable health information.

Blood is the gold standard for measuring our biochemistry. Our biochemistry gives information about normal biological processes, pathogenic processes, and even pharmacologic responses to a therapeutic intervention. The next generation of wearable devices must be able to continuously measure biochemistry in real-time. However, continuous sampling is a problem for biofluids such as blood, which requires invasive, needle-based draws at discrete time points. However, other biofluids such as sweat, saliva, and tears contain analytes that can be continuously measured non-invasively. These non-invasive sensing mechanisms are limited because certain analytes are present in blood at more physiologically relevant concentrations compared to non-invasively accessible biofluids (e.g., sweat, saliva, and tears).

SUMMARY OF THE INVENTION

Embodiments of the disclosed invention function to increase the concentration of analytes in biofluids by increasing the paracellular permeability of the epithelial barrier using at least one paracellular-permeability-enhancing agent. This can be applied to epithelia such as, but not limited to, the epidermis, the sweat gland epithelium, and the oral mucosa. Examples of paracellular-permeability-enhancing agents to be used include but are not limited to chelators, lipids, and proteins. In an embodiment, the paracellular-permeability-enhancing agent can be delivered topically. Since these agents are usually charged, in another embodiment, the agent can be delivered using iontophoresis. This is advantageous in cases where simple diffusion is incapable of delivering enough agent to produce an effect. In another embodiment, analyte-rich interstitial fluid can be actively flowed into the secreted biofluid via electro-osmotic flow induced by reverse iontophoresis.

Modifying the paracellular permeability of the epithelial barrier has been extensively studied for pharmacological purposes such as to increase drug absorption in gut epithelia or transdermal drug absorption through the epidermis. However, modifying the paracellular permeability of epithelial tissues can also be useful in non-invasive biosensing applications to enhance extraction of analytes. Thus, because blood and interstitial fluid (ISF) contain analytes at more physiologically relevant concentrations compared to non-invasively accessible biofluids (e.g., sweat, saliva, and tears), enhancing paracellular permeability can improve the measurement of the target analyte(s).

In some instances, an increase in paracellular permeability alone will not be sufficient to enhance analyte access through epithelial tissues. ISF is under negative hydrostatic pressure, so an active method of flowing ISF from the basolateral side to the apical side of the epithelium may be necessary. This active fluid flow can be established using electro-osmotic flow induced by reverse iontophoresis. The electrical double layer needed for electro-osmosis is formed by the negatively-charged epithelial cell surface (due to the carboxylic acid moieties within glycans [including glycosaminoglycans] and proteins [including collagen]) interacting with the positively-charged ions in the extracellular matrix (including sodium and potassium). When an external electric field is applied, cations in both the double layer and bulk solution will move toward the electrochemical cathode, an effect known as reverse iontophoresis. Electro-osmosis describes the phenomenon in which the movement of the cations within the double layer causes the bulk solution to move toward the electrochemical cathode. Therefore, reverse-iontophoresis-induced electro-osmotic flow can be used to drive the flow of analytes from blood and ISF into biofluids that can be non-invasively measured outside of the body.

Increasing the concentration of analytes that can be extracted through epithelial tissues will improve the detection of previously hard-to-detect analytes, making non-invasive biosensing a more viable option for health monitoring.

BRIEF DESCRIPTION OF THE DRAWINGS

The objects and advantages of the disclosed invention will be further appreciated in light of the following detailed descriptions and drawings in which.

DEFINITIONS

Figure 1A:
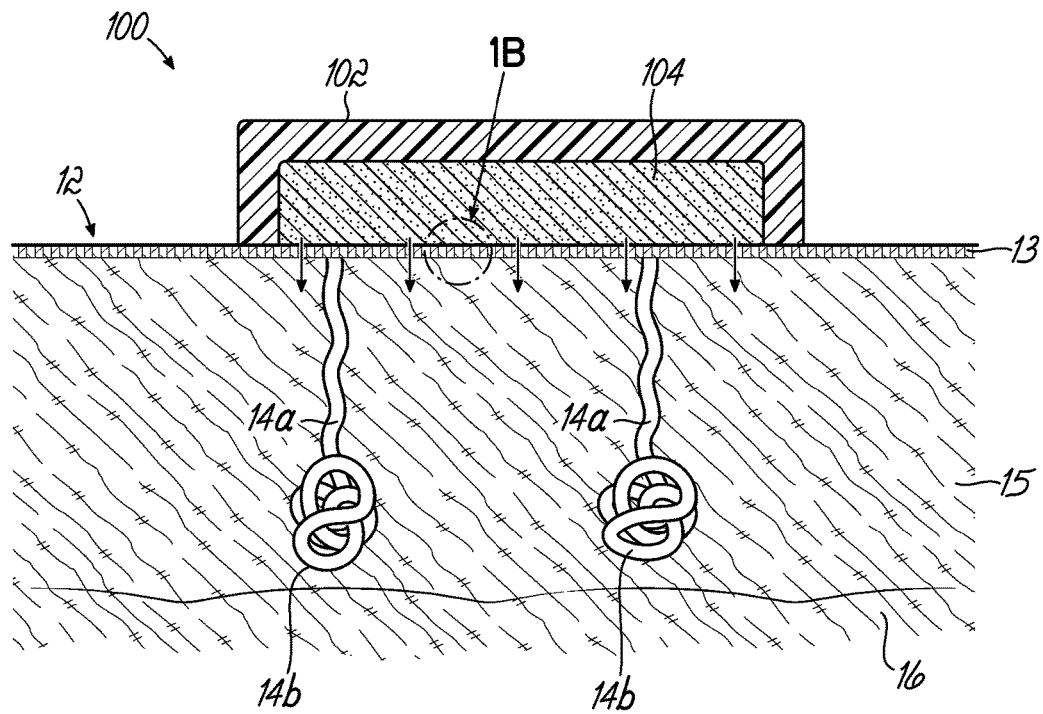
FIGS. 1A and 1C are cross-sectional views of a device according to an embodiment of the disclosed invention capable of both delivering a paracellular-permeability-enhancing agent topically and collecting the resulting analyte-rich fluid extracted from the apical surface of the epithelium.
Figure 1B:
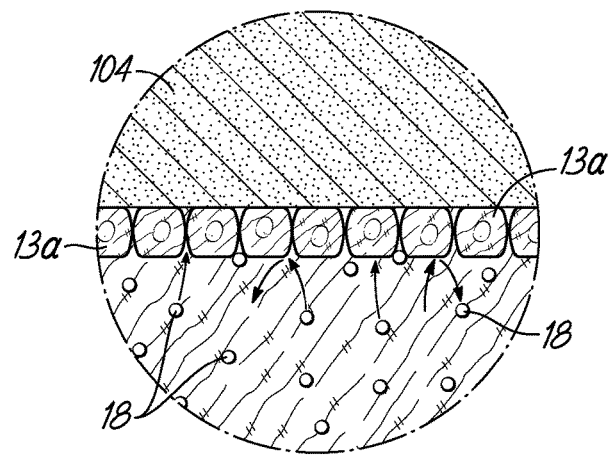
FIGS. 1B and 1D are enlarged cross-sectional views of the epidermis before and after enhancement of the paracellular permeability by the device of FIGS. 1A and 1C, respectively.
Figure 1C:
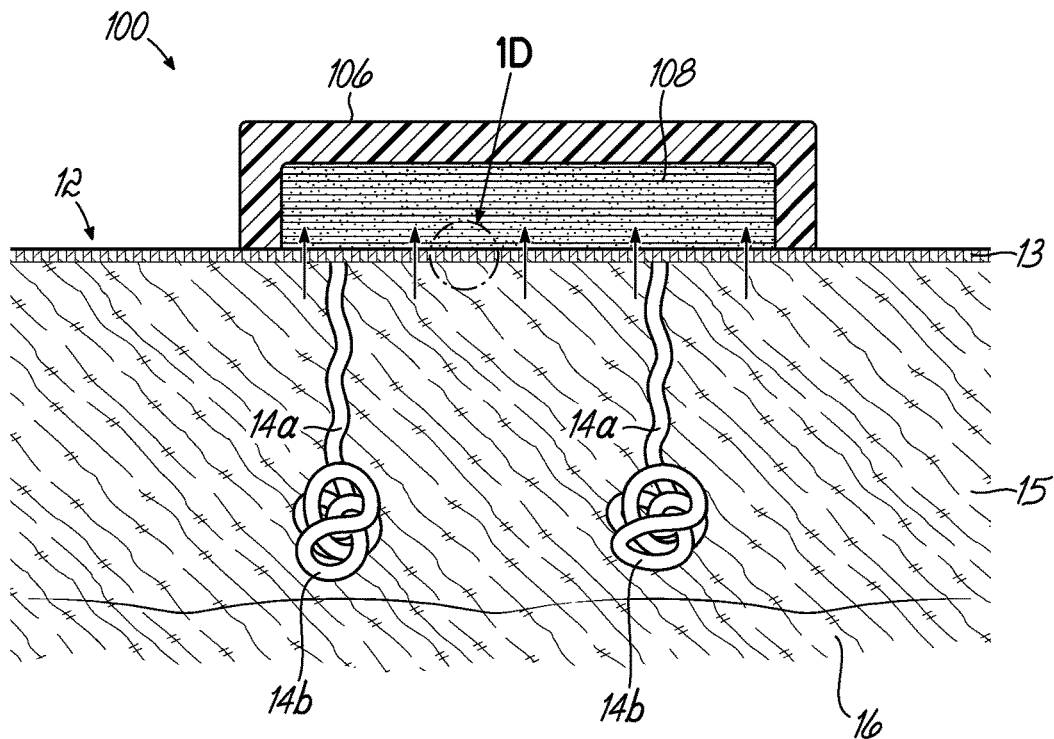

As used herein, "interstitial fluid" or "tissue fluid" is a solution that bathes and surrounds tissue cells. The interstitial fluid is found in the interstices—the spaces between cells. Embodiments of the disclosed invention focus on interstitial fluid found in the skin and, particularly, interstitial fluid found in the dermis. In some cases where interstitial fluid is emerging from sweat ducts or salivary ducts, the interstitial fluid contains some sweat or saliva as well, or alternately, sweat or saliva may contain some interstitial fluid.

As used herein, "biofluid" is a fluid that is comprised mainly (e.g., 50% by volume or greater) of interstitial fluid, sweat, or saliva as it emerges from the sweat ducts or salivary glands. For example, a fluid that is 45% interstitial fluid, 45% sweat, and 10% blood is a biofluid as used herein. For example, a fluid that is 20% interstitial fluid, 20% sweat, and 60% blood is not a biofluid as used herein. For example, a fluid that is 100% sweat or 100% interstitial fluid is a biofluid. A biofluid may be diluted with water or other solvents inside a device because the term biofluid refers to the state of the fluid as it emerges from the skin. Generally, as compared to blood, sweat is dilute of large sized analytes (e.g., greater than 1000× for proteins, etc.) and to a lesser extent, as compared to blood, interstitial fluid is dilute for some larger sized analytes (e.g., 10-100× or more or less depending on the specific analyte, current density, etc.).

As used herein, "advective transport" is a transport mechanism of a substance or conserved property by a fluid due to the fluid's bulk motion.

As used herein, "reverse iontophoresis" is a subset of "iontophoresis" and is a technique by which electrical current and electrical field cause molecules to be removed from within the body by electro-osmosis and/or iontophoresis. Although the description below focuses primarily on electro-osmosis, the term "reverse iontophoresis" as used herein may also apply to flux of analytes brought to or into a device of the disclosed invention, where the flux is in whole or at least in part due to iontophoresis (e.g., some negatively charged analytes may be transported against the direction of electro-osmotic flow and eventually onto a device according to an embodiment of the disclosed invention). Electro-osmotic flow (synonymous with electro-osmosis or electro-endosmosis) is the motion of liquid induced by an applied potential across a porous material, capillary tube, membrane, microchannel, or any other fluid conduit. Because electro-osmotic velocities are independent of conduit size, as long as the electrical double layer is much smaller than the characteristic length scale of the channel, electro-osmotic flow is most significant when in small channels. In biological tissues, the negative surface charge of plasma membranes causes accumulation of positively charged ions such as sodium. Accordingly, fluid flow due to reverse iontophoresis in the skin or oral mucosa is typically in the direction of where a negative voltage is applied (i.e., the advective flow of fluid is in the direction of the applied electric field).

As used herein, the term "iontophoresis" may be substituted for "reverse iontophoresis" in any embodiment where there is a net advective transport of biofluid to the surface of the skin. For example, if a flow of sweat exists, then negatively charged analytes may be brought into the advectively flowing sweat by iontophoresis. The net advective flow of sweat would typically be needed, because in this case, a net electro-osmotic fluid flow would be in the direction of sweat into interstitial fluid (and without a net advective flow of sweat, the sweat would be lost, and there would be no pathway for transporting the analyte to at least one sensor). Furthermore, because "reverse iontophoresis" is a subset or more specific form of "iontophoresis", the term "iontophoresis" may refer to both "reverse iontophoresis" and "iontophoresis". The terms "reverse iontophoresis" and "iontophoresis" are interchangeable in the disclosed invention.

As used herein, the term "analyte-specific sensor" is a sensor specific to an analyte and performs specific chemical recognition of the presence or concentration of the analyte (e.g., ion-selective electrodes, enzymatic sensors, electrochemical aptamer-based sensors, etc.). For example, sensors that sense impedance or conductance of a fluid, such as biofluid, are excluded from the definition of "analyte-specific sensor" because sensing impedance or conductance merges measurements of all ions in biofluid (i.e., the sensor is not chemically selective; it provides an indirect measurement). Sensors could also be optical, mechanical, or use other physical/chemical methods which are specific to a single analyte. Further, multiple sensors can each be specific to one of multiple analytes.

As used herein, a paracellular-permeability-enhancing agent is an agent that increases the paracellular permeability of an epithelial barrier such that extracted analyte concentration is increased by at least 2× compared to the case of using no paracellular-permeability-enhancing agent. For example, a sweat sensing device for glucose or for albumin could collect a sweat sample with have a concentration of 25 μM or 120 ng/mL, respectively, and with application of the paracellular-permeability-enhancing agent as taught herein, these concentrations in a sweat sample could be increased to greater than 1000 μM or greater than 280 ng/mL, respectively, which is greater than a 2× increase.

DETAILED DESCRIPTION OF THE INVENTION

While some analytes are actively secreted with biofluids (e.g., sweat, saliva, and tears), most are produced elsewhere in the body and must diffuse into the biofluid from blood or interstitial fluid (ISF). The circulatory system serves as the fastest way to circulate biomarkers throughout the body, allowing blood to be the gold-standard for biomarker detection. Epithelial tissue is usually heavily vascularized with capillaries, potentially providing an indirect path to sample blood. The function of the capillaries is to exchange nutrients and signaling molecules and to remove waste. These functions require a degree of natural permeability, which allows analytes to pass from blood into the fluid surrounding the extracellular space, ISF. Because of the permeability of capillaries, ISF has similar concentrations of analytes compared to blood after some amount of time. For example, ISF glucose concentrations match that of blood after about 15 minutes. Although surrounded by analyte-rich blood and ISF, biofluids such as sweat, saliva, and tears are separated from blood and ISF by an epithelial layer, which acts as a barrier for analyte entry, diluting the concentration of analytes of interest and making them difficult to detect by current sensing and analysis methodologies.

There are two routes of entry of analytes from the basolateral side of an epithelium to the apical side: transcellular (through the cells) and paracellular (between the cells). The lipid bilayer forms a continuous barrier preventing transcellular transport except for small and/or hydrophobic molecules. Lipid bilayers prevent diffusion of charged molecules and large (e.g., greater than 500 Da) polar molecules, including biopolymers, and retard diffusion of polar molecules such as water, urea, and glucose. Small hydrophobic molecules, such as cortisol and other hormones, can more readily diffuse across the lipid membrane to enter biofluids, but will still diffuse more slowly than in the absence of the bilayer. Paracellular pathways, in comparison, are discontinuous and can allow larger molecules to diffuse through, although the network of proteins and glycans significantly slows paracellular diffusion. In particular, cells in the epithelium layer are joined near their apical surface by tight junctions that function as a barrier, limiting diffusion of analytes from the interstitial fluid surrounding the basolateral side of the cells. The paracellular space between these cells is 10's of nanometers wide, leaving plenty of room for large analytes to pass. However, tight junctions link neighboring cell membranes to form a seal that allows relatively free passage of water and monoatomic ions but tends to filter other substances, reducing effective concentrations observed in the secretory biofluid by at least 10×, and more often 100 to 1000 to greater than 10,000×. To modulate the paracellular permeability, paracellular-permeability-enhancing agents act as extracellular signals that regulate the remodeling of the tight junctions between the cells. The addition of these paracellular-permeability-enhancing agents results in increased permeability along the paracellular pathway for large, uncharged, polar molecules as well as for charged molecules.

The extracellular signal to be modulated may vary based on the intended application. Exemplary extracellular signals that may be regulated to increase paracellular permeability include, but are not limited to, the presence and amount of extracellular calcium, the binding of fatty acids to free fatty acid receptors including G-protein-coupled receptors (GP-CRs), and the presence and amount of pathogenic proteins or lipids (e.g., oleic acid, caprylic acid, and lysophosphatidic acid (LPA)). Exemplary pathogenic proteins include endotoxins, such as the *Zonula occludens* toxin (Zot) produced by *Vibrio cholera*. Further, it should be recognized that the agent used for enhancing paracellular permeability may vary based on intended application and the extracellular signal being regulated.

An exemplary paracellular-permeability-enhancing agent is a chelator. Chelators bind metal ions and can be used to sequester extracellular metal ions causing a local drop in the concentration of the metal ions. Chelators having different binding affinities for various cations based on their molecular structure and/or pH may be used. Exemplary chelators include polycarboxylates and polycarboxylic acids, such as ethylenediaminetetraacetic acid (EDTA) and citric acid, as well as their conjugate bases. Both EDTA and citric acid bind to calcium in a roughly 1:1 molar ratio depending on the pH of the solution. For example, the extracellular calcium concentration within the sweat lumen is roughly 1-2 mM, and around 1-2 mM of either EDTA or citric acid may be used to sufficiently sequester the extracellular calcium ions due to the tight affinity of chelators for divalent cations. This drop in calcium concentration has been demonstrated to trigger an increase in clathrin-mediated endocytosis of tight junction proteins connecting epithelial tissues. Both EDTA and citric acid (and its citrate derivatives) have been reviewed by the Cosmetic Ingredient Review (CIR) and are used at concentrations up to 70 mM and 520 mM, respectively, which is well below the concentration used to fully sequester the extracellular calcium in biofluids.

Another exemplary paracellular-permeability-enhancing agent is a protein, such as an endotoxin produced by pathogenic bacteria or fungi. Zot, produced by *Vibrio cholerae*, binds to intestinal epithelial Zot receptors to activate protein kinase C alpha (PKCα), which causes an increase in paracellular permeability. An effective dose of a protein paracellular-permeability-enhancing agent may be in a picomolar or micromolar range. For example, an effective dose may be in a range of 1 pM to 100 pM.

Another exemplary paracellular-permeability-enhancing agent is a lipid. Lipids, such as oleic acid (C18:1) or caprylic acid (C10), bind to free fatty acid receptors on the cell surface. These binding events trigger signal generation and transduction via secondary messengers inside the cell to trigger a host of cellular events. For example, binding of oleic acid to G-protein coupled receptors (GPCR) ($G_q$) activates phospholipase C (PLC) which phosphorylates phosphatidylinositol (4,5)-bisphosphate ($PIP_2$) into phosphatidylinositol (3,4,5)-trisphosphate ($PIP_3$). $PIP_3$ triggers the release of calcium stores in the endoplasmic reticulum. The rise in intracellular calcium levels causes the contraction of calmodulin-dependent actin microfilaments resulting in an enhanced tight junction permeability. Oleic acid and caprylic acid are major constituents of olive oil and milk fat, respectively. Both are classified as Generally Recognized as Safe (GRAS) by the FDA. Other lipids have been identified (e.g., lysophosphatidic acid (LPA)) that increase paracellular permeability but are not currently FDA approved. An effective dose of a lipid or protein paracellular-permeability-enhancing agent may be in a picomolar, micromolar, or millimolar range. For example, an effective dose may be in a range of 20 pM to 30 mM.

Figure 1D:
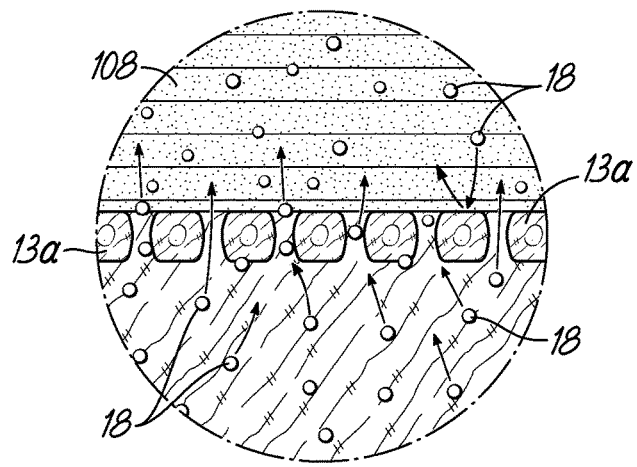

With reference to FIGS. 1A-1D, in an aspect of the disclosed invention, a device 100 delivers a paracellular-permeability-enhancing agent through diffusion. The device 100 is positioned on the skin 12 composed of the epidermis 13, the dermis 15, and layers of skin below the dermis 16. The skin 12 contains multiple sweat glands 14 each containing a ductal lumen 14a and a secretory coil 14b. The device 100 delivers a paracellular-permeability-enhancing agent topically by securing a component 102 including an agent-containing gel or solution 104 against the skin 12 (i.e., the apical surface of the epidermis 13). Prior to the agent enhancing the paracellular permeability, the epithelium cells 13a are packed tightly together, which prevents certain analytes 18 (e.g., large, polar analytes) from passing through the epidermis 13. The agent is allowed time to diffuse into the skin 12 and trigger the remodeling of the tight junctions resulting in increased paracellular permeability. Once permeability is established, a component 106 with absorbent disks 108 may be used to collect the analytes 18 that are now able to pass through the epidermis 13, as shown in FIG. 1D. The absorbent disks 108 are made of a material with low non-specific absorption that may have near 100% sample recovery and may have a shape other than a disk. A suitable material includes SEFAR NITEX, which is a polyamide-based non-woven, hydrophilic mesh with low surface area and low non-specific binding of analytes such as proteins. Other suitable materials include filter paper, tech wipes, or rayon. The material for the absorbent disks 108 may be surface treated to prevent non-specific binding to analytes. This example paracellular-permeability-enhancing feature has a discrete permeability enhancing step, which is separate from the collection step. It should be recognized that other methods of applying a paracellular-permeability-enhancing agent are possible, and an increase in permeability can occur simultaneously with collection and/or sensing as described below.

Figure 2:
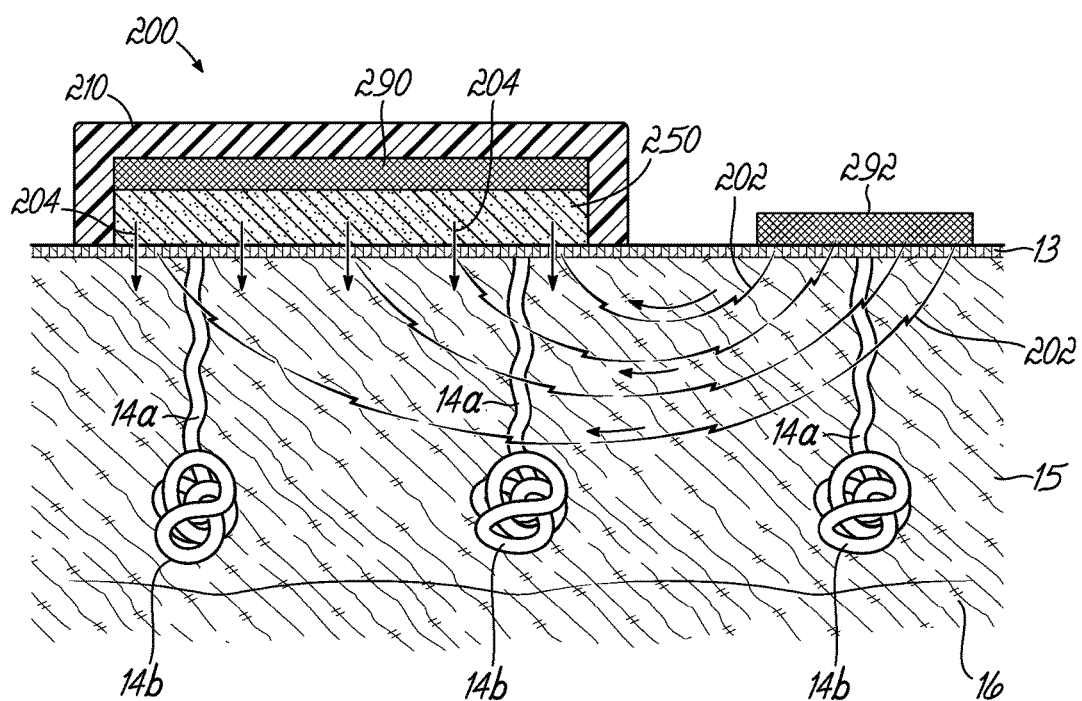
FIG. 2 is a cross-sectional view of a device according to an embodiment of the disclosed invention capable of delivering a paracellular-permeability-enhancing agent using iontophoresis.

With reference to FIG. 2, in another aspect of the disclosed invention, a device 200 actively delivers a paracellular-permeability-enhancing agent using iontophoresis. Iontophoresis is the movement of a charged molecule in response to an electric field (lines 202). The movement of molecules is directly related to the current. Since iontophoresis can only move charged molecules, only charged paracellular-permeability-enhancing agents can be delivered in this manner. Most paracellular-permeability-enhancing agents are charged: chelators have a negative charge, free-fatty acids have a negative charge associated with the acid moiety, and proteins usually have some charge. Iontophoresis is especially useful when the epithelium to be targeted is not directly accessible as in the case of the sweat gland ductal epithelium. The secretory coil 14b generates a positive pressure pushing sweat up and out to the surface of the skin 12, severely limiting the amount of paracellular-permeability-enhancing agent able to diffuse into the ductal lumen 14a. To counteract that, a reservoir 250 includes an agent-containing gel or solution and is placed on the surface of the skin 12. The device 200 includes an electrode 290, which is in electrical contact with the agent-containing gel or solution in the reservoir 250, and a counter electrode 292. The counter electrode 292 is situated on the surface of the skin 12 adjacent to and spaced apart from reservoir 250 and electrode 290. The device 200 further includes a substrate 210 around the reservoir 250 and the electrode 290. The material for the substrate 210 is impermeable to biofluids and may be, for example, a polyimide film or polyethylene terephthalate (PET). The substrate 210 may include an adhesive backing made of, for example, a hypoallergenic acrylate or other similar medical-grade material. A constant current is applied between the electrodes 290, 292. The current to be applied takes into consideration the area over which it will be applied. As a result, the current density is usually considered. The minimum current density used to drive the paracellular-permeability-enhancing agent depends at least in part on the amount of calcium re-entering the system as well as the concentration of competing negatively-charged ions and molecules in solution. The maximum current that would be applied depends on safety and user comfort. In various embodiments, the current density is less than 0.25 mA/cm$^2$ or in a range between 0.01 mA/cm$^2$ and 0.25 mA/cm$^2$. The voltage needed to produce these current densities is a function of the resistance of the skin. The resistance of the skin when sweating is lower than the resistance when the skin is dry. Because the device 200 is used when the skin is sweating, the voltages needed to produce these current densities are less than 30 V. The voltage may be within the range of 5-15 V. The electrode 290 in electrical contact with the agent-containing gel or solution is configured to have the same charge compared to the agent. For example, to deliver citric acid, a negatively-charged chelating agent, the electrode 290 in electrical contact with citric acid will be negative. This will repel the citric acid down into the ductal lumen 14a (arrows 204) so that it can have maximum effect. As a result, the luminal calcium level will decrease, triggering an increase in paracellular permeability. Although not shown, it should be recognized that this device may also include a biofluid collection and/or sensing component.

In another aspect of the disclosed invention, the effectiveness of a chelator is proportional to the amount of calcium ions sequestered. For example, consider the case of sweat. As described above, chelators (e.g., citric acid and EDTA) sequester calcium at a roughly 1:1 molar ratio. The amount of calcium present in the sweat can be determined from known quantities—volume of the sweat gland and concentration of calcium in sweat, for example. This yields the amount of calcium within a single, saturated sweat gland. Iontophoresis is usually performed on an area that can contain hundreds of sweat glands. Knowing the size of the area where iontophoresis is performed and the density of sweat glands within that area yields the number of sweat glands within the treatment area. The product of the number of sweat glands and the amount of calcium per sweat gland is the total amount of calcium that can be sequestered by chelators. Note that, as time goes on, the sweat gland will continue to produce sweat containing additional calcium. The effectiveness of the chelation treatment relies on the total percent sequestration of calcium within the sweat glands. The effectiveness of the treatment will be reversible as the chelating agent is depleted and calcium from the interstitial fluid and from the body is pulled into the sweat gland.

The following first principles calculation is provided to help illustrate an embodiment of the disclosed invention and is not comprehensive or limiting in any manner. According to documentation provided from Moor Instruments, dosage of an agent applied using iontophoresis can be calculated under a strict set of assumptions: 1) all electrical current is due to the passage of agent ions and 2) one monovalent agent molecule is passed into the tissue per electron charge. The relationship between moles of the agent that is applied through iontophoresis, the applied current, and the duration is approximated below in Equation 1.

$$\text{Moles of agent iontophoresed (mol)} = \frac{\text{Current }(A) \times \text{Duration }(s)}{\text{Faraday constant}\left(\frac{C}{\text{mol}}\right)}$$

In an embodiment, citric acid can be iontophoretically delivered using a current of 2 mA for 1 hour over an area of 1.89 cm$^2$. Within this area are roughly 280 sweat glands, assuming a sweat gland density of 150 glands/cm$^2$. Using Equation 1, approximately 74.6 µmol of citric acid would be delivered during this treatment. Iontophoresis as prescribed above would deliver an electric charge of 7.2 C (i.e., a current of 2 mA over the duration of 1 hour provides a charge of 7.2 C). The dominant species of citric acid has one negative charge at sweat pH. Citric acid binds calcium in approximately 1:1 molar ratio, meaning that about 75 µmol of calcium would be sequestered. Assuming a sweat gland volume of around 50 µL and a concentration of calcium of 2 mM, enough citric acid will be delivered to sequester the calcium of nearly 750 sweat glands. This is over 2.5× what is necessary for the assumed 280 sweat glands, helping to account for the limitations of the assumption set as described above. In practice, agents may be delivered in excess of 10×, 100×, or even 1000× what is necessary to produce a paracellular permeability enhancement effect. The calculation above makes the assumption that there are no similarly-charged molecules or ions that will compete with the agent. In addition, this calculation does not take into account the rush of calcium from ISF that will inevitably migrate into the ductal lumen 14a to replace the chelated calcium. As a result, embodiments of the present invention include delivery of excess agent, multiple agent deliveries, or continuous agent delivery.

Figure 3A:
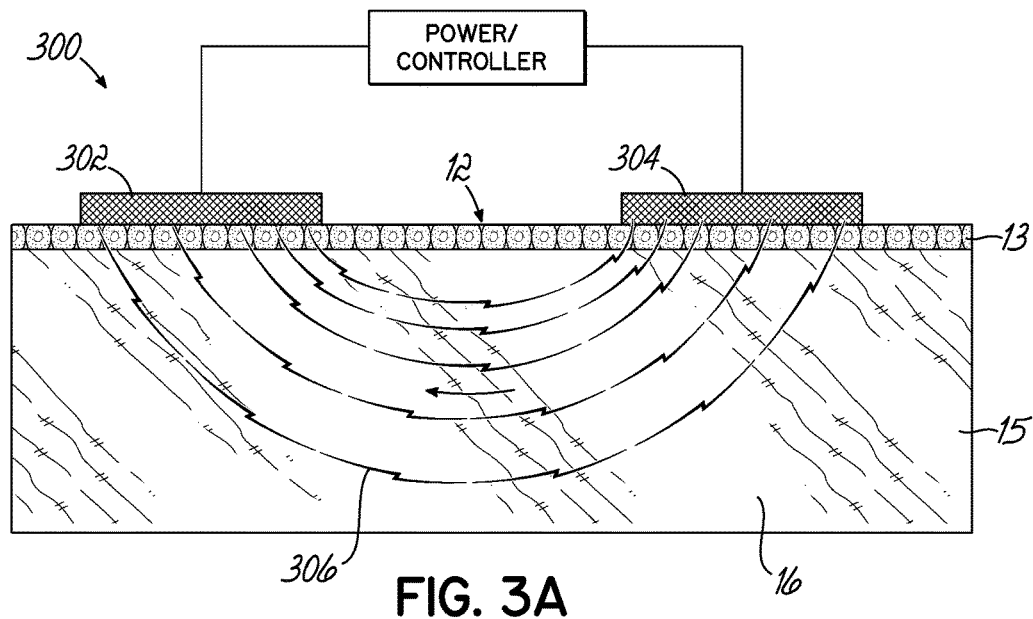
FIG. 3A is a cross-sectional view of a mechanism capable of causing reverse-iontophoresis-induced electro-osmotic flow according to an embodiment of the disclosed invention.
Figure 3B:
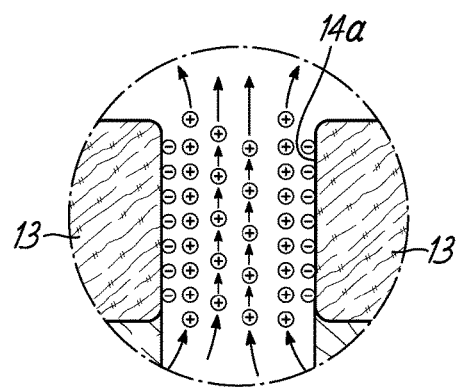
FIG. 3B is a cross-sectional view of the ductal lumen shown during reverse-iontophoresis-induced electro-osmotic flow caused by the device of FIG. 3A.

In an aspect of the disclosed invention, an increase in paracellular permeability is combined with the principals of reverse iontophoresis and electro-osmosis to magnify the movement of analytes from blood and ISF through the epithelial layer and into an advective flow of the biofluid (e.g., sweat or saliva). With reference to FIGS. 3A and 3B, in an embodiment, a reverse iontophoresis mechanism 300 includes two electrodes 302, 304 spaced apart on the skin 12. The paracellular permeability may first be enhanced using an agent as described herein. In the case of inaccessible epithelia like sweat gland ductal epithelium, the voltage applied by the electrodes 302, 304 on the surface of the skin 12 will be transferred by the conductive sweat down to the ductal lumen 14a. The voltage may be relatively low such as, for example, about 5 V, less than or equal to 15 V, or less than or equal to 30 V. In an embodiment, the voltage may be in a range of about 5-30 V or a range of about 5-15 V. The electrical double layer needed for electro-osmosis is formed by the negatively-charged cell surface (i.e., due to the carboxylic acid moieties within glycans, such as glycosaminoglycans, and proteins, such as collagen) interacting with the positively-charged ions in the extracellular matrix. When an external electric field (lines 306) is applied by the electrodes 302, 304, cations in both the double layer and bulk solution will move toward the electrochemical cathode. The movement of the cations within the double layer causes the bulk solution to move toward the electrochemical cathode. Thus, in an embodiment, an epithelium is treated with an agent to increase paracellular permeability followed by electro-osmosis to drive blood and ISF to the apical surface of the epithelium. The increased paracellular permeability and the reverse-iontophoresis-induced electro-osmotic flow may increase a concentration the analyte of interest in the advective flow of the biofluid by 2×× or greater, 10× or greater, 50× or greater, and up to 1000×. For example, the increase may be in a range of 2-1000×.

In an aspect of the disclosed invention, the amount of the paracellular-permeability-enhancing agent that is delivered to the sweat gland is proportional to the total current during iontophoresis. The total dose is at least partially dependent on the electric field strength, the concentration of analyte, and the total duration of the applied iontophoresis. For example, a paracellular-permeability-enhancing agent of interest is repulsed from the electrochemical cathode due to the agent's negative charge and migrates at a velocity based on the local electric field it is experiencing, its molecular size and shape, and its mass-to-charge ratio. As the charge on the agent becomes greater as a function of pH (i.e., moving from monosodium to disodium citrate) or as a function of the agent, the applied force increases proportionally, increasing the velocity and thus the flux of the agent toward the epithelium.

Both iontophoresis and reverse-iontophoresis-induced electro-osmosis require electrical stimulation of the epithelium. If electrical contact is poor, then the surface area stimulated will be smaller than expected, and the resulting current density may be higher than anticipated. The two major concerns with electrical stimulation are the possibilities of 1) electrical and/or 2) pH-induced acid/base damage. Electrical damage is caused by Joule heating effects as a result of an electric current flowing through the epithelium. These types of damage are largely avoidable by staying within safe current density limits set out by FDA-approved products designed to provide on-body electrical stimulation, such as the Nanoduct (0.26 mA/cm$^2$). The electrolysis of water results in pH-induced burns, which occurs when voltages applied during iontophoresis or reverse iontophoresis exceed that of the standard electrode potential of water (−1.23 V). At the electrochemical cathode, reduction of water will produce hydrogen gas and hydroxide ions, increasing the basicity of the water ($2H_2O(l)+2e^- \rightarrow H_2(g)+2 OH^-(aq)$). At the electrochemical anode, oxidation of water will produce oxygen gas and hydrogen ions, increasing the acidity of the water ($2H_2O(l) \rightarrow O_2(g)+4H^+(aq)+4e^-$). It is important to consider how the applied current will affect the chemical composition including pH to avoid any injury. Also, the safe current density assumes good electrode contact with the entire area.

The duration of the effect produced by a single delivery of a paracellular-permeability-enhancing agent may not last long enough to increase the concentration of analytes during the entire collection or sensing period, warranting additional dosing events or continuous delivery. In addition, ISF has a negative hydrostatic pressure, meaning that an increase in paracellular permeability alone may not be sufficient to bring in analytes from ISF. As a result, simultaneous iontophoretic delivery of agent and reverse-iontophoresis-induced electro-osmotic flow may be needed depending on the particular application and the biofluid to be sensed.

Figure 4:
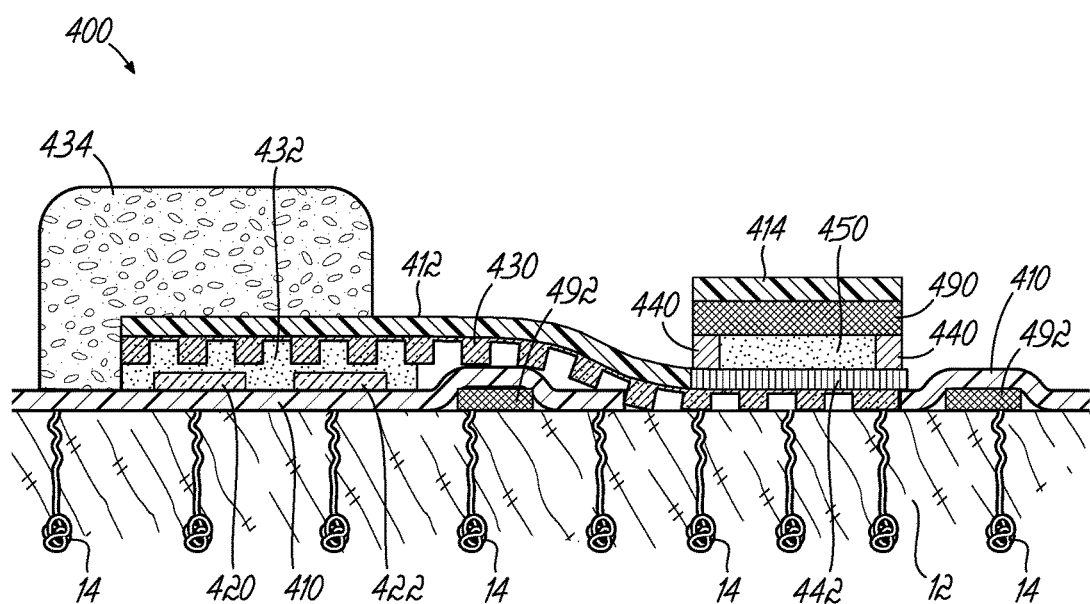
FIG. 4 is a cross-sectional view of a device according to an embodiment of the disclosed invention capable of delivering a paracellular-permeability-enhancing agent via iontophoresis and simultaneously performing reverse iontophoresis to actively flow analytes from blood and ISF into the device to be sensed by sensors in real time.

With reference to FIG. 4, in an embodiment, a device 400 is capable of delivering a paracellular-permeability-enhancing agent, generating reverse-iontophoresis-induced electro-osmotic flow, and sensing the resulting fluid in real-time, continuously. The device 400 includes a reservoir 450 including an agent-containing gel or solution, an electrode 490 in electrical contact with the agent in the reservoir 450, and a counter electrode 492. The electrodes 490, 492 are adapted to deliver the agent iontophoretically and adapted to increase a concentration of the analyte of interest in an advective flow of the biofluid by at least 2×. The reservoir 450 is bordered vertically by sidewalls 440 and on the top by the electrode 490. The material for the sidewalls 440 is impermeable to biofluid and to the agent even when iontophoresis is applied; the material may be similar to that described for the substrate 210. A membrane 442 is positioned between the reservoir 450 and the skin 12 and prevents the agent from diffusing out and onto the skin without iontophoresis. The membrane 442 is only slightly permeable to the agent so that there is limited or no diffusion without the application of iontophoresis. When an iontophoretic voltage is applied, the agent has sufficient energy to pass through the membrane 442. Suitable materials for the membrane 442 include cellulose acetate, cellulose ester, polyamide, and track-etched polycarbonate membranes.

Still referring to FIG. 4, for sensing sweat, the device 400 includes analyte-specific sensors 420, 422 and sweat sample management components 430, 432, 434. The component 430 acts as a sweat sample collector and transports sweat from the surface of the skin 12. A portion of the sample collector 430 may be positioned between the electrode 490 and the skin 12 because the analyte-rich advective flow of biofluid is drawn toward the electrode 490. The component 432 acts as sample coupler and transports sweat from the sample collector 430 across the sensors 420, 422. The component 434 acts as a sample pump and moves excess or old sweat from the sample collector 430 and the sample coupler 432. The sample pump 434 may be designed to store 10's to 100's of μL of old sweat. Suitable materials for the sweat sample management components 430, 432, 434 include, for example, a textile; stacks of hydrophilic membrane filters; hydrophilic beads (e.g., commercial monodisperse Reade Silica powder); a longer-chain length hydrogel; a porous polymer; nano-cellulose; and microfluidic channels, among other suitable materials. The device 400 further includes substrates 410, 412, 414, which may include adhesive backings as described above. The substrate 410 secures the counter electrode 492 and separates the sensors 420, 422 from the skin 12. The substrates 412 prevent evaporation of the sweat from the top of the sample collector 430 and sample coupler 432. Although the illustrated embodiment includes iontophoretic application of the paracellular-permeability-enhancing agent and sweat sensing, it should be recognized that a device may include sweat sensing along with a different technique used to apply a paracellular-permeability-enhancing agent (e.g., topically).

In use, the paracellular permeability is enhanced and then the sweat is sensed using the device 400. First, the paracellular-permeability-enhancing agent in the reservoir 450 is iontophoretically delivered to the skin 12. An applied electric field between the electrodes 490, 492 drives the agent through the membrane 442 and into the epidermis 13. When the electric field is applied, fluid is drawn to the negative electrode due to reverse-iontophoresis-induced electro-osmosis. Thus, paracellular-permeability-enhancing agents that are negatively charged will be delivered while the electro-osmosis is causing an active flow of the analyte-rich fluid into the sweat gland ductal epithelium. For reverse iontophoresis, the current density may be in the $\mu A/cm^2$ range, far below the 0.25 $mA/cm^2$ precedent set by the FDA-approved Nanoduct device, which is designed to work on dry, non-sweating skin. Once sweating begins, the sweat glands 14 are saturated with highly conductive sweat and allow the applied current to be conducted much deeper into the tissue, closer to nerves. As the sweat emerges onto the skin 12, the sample collector 430 transports the sweat towards the sensors 420, 422. The sample coupler 432 transports the sweat from the sample collector 430 to the sensors 420, 422 to be sensed. After the sweat has been sensed, the sample pump 434 draws the old sweat away from the sensors 420, 422 to prevent contamination of new sweat samples. In an aspect of the disclosed invention, depending on the application and configuration of the device, a net advective flow of biofluid from the skin 12 to the sensor(s) in the device may be required for the sensor(s) to sense the desired analytes in the biofluid.

Enhancing the paracellular permeability and inducing the electro-osmotic flow may be accomplished in series or in parallel (e.g., simultaneously). In an embodiment, the paracellular-permeability-enhancing agent may be first applied to the epithelial tissue and then the electro-osmotic flow may be induced (e.g., as described in relation FIG. 3). In another embodiment, for example with reference to FIG. 4, the application of a current between the electrodes 490, 492 iontophoretically delivers the agent and induces electro-osmotic flow simultaneously. Further, enhancing the paracellular permeability and inducing the electro-osmotic flow may each be accomplished during one or more discrete time periods or continuously.

While the above embodiments are described relative to sweat, embodiments of the disclosed invention are not so limited. For example, with reference again to FIG. 4, the device 400 could be placed in the mouth with the skin 12 representing the tissue lining the mouth. In other words, when the biofluid to be sensed is saliva, references to "the skin" may include the oral mucosa or other tissue in the mouth where salivary glands exist (e.g., under the tongue). Saliva generation rates are generally much higher than sweat generation rates. Finally, because substantial portions of the epithelial tissue in oral mucosa lacks a keratinized layer, fewer cells exist separating the superficial layer (mucosal layer) from the ISF and/or capillaries. This likely means that paracellular permeability enhancement is not limited solely to the salivary gland, but can be effective for the entire non-keratinized mucosal layer. Thus, topical delivery of the agent may provide the desired effect without the use of iontophoretic delivery. In various embodiments, the paracellular-permeability-enhancing agent may be applied topically, such as via a lozenge or a mouthwash, and/or iontophoretically. After application of the agent, fresh saliva could be provided to sensors quickly and be displaced as new saliva appears without the function of a wicking component for real-time sensing applications. Saliva monitoring devices could be mechanically less comfortable or ergonomic for longer term use than sweat monitoring devices. However, because saliva is always generating in the mouth, it could be suitable for one-time biomarker analysis. As a result, a device that enhances paracellular permeability and collects the biofluid for later analysis (e.g., device 100) may be useful.

Certain embodiments of the disclosed invention show sensors as simple individual elements. It is understood that many sensors require two or more electrodes, reference electrodes, or additional supporting technology or features which are not explicitly described in the description herein. Sensors are preferably electrical in nature, but may also include optical, chemical, mechanical, or other known biosensing mechanisms. Sensors can be in duplicate, triplicate, or more, to provide improved data and readings. The above description of various embodiments of the disclosed invention may not include a description of each and every component that may be used for the functioning of the devices depending on the application (e.g., a battery or a controller), although it should be recognized that such components are included in the scope of the disclosed invention. For the purpose of brevity and to provide a focus on the inventive aspects described above, such components are not explicitly shown in the diagrams or included in the relevant description.

While specific embodiments have been described in considerable detail to illustrate the disclosed invention, the description is not intended to restrict or in any way limit the scope of the appended claims to such detail. The various features discussed herein may be used alone or in any combination. Additional advantages and modifications will readily appear to those skilled in the art. The disclosed invention, in its broader aspects, is therefore not limited to the specific details, representative apparatus and methods, and illustrative examples shown and described. Accordingly, departures may be made from such details without departing from the scope of the general inventive concept.

What is claimed is:

1. A device comprising:
   an agent for enhancing a paracellular permeability of a device wearer's epithelial tissue;
   an iontophoresis electrode and a counter electrode, which are configured to increase the concentration of at least one analyte in a biofluid by the following: using iontophoresis to transport the agent into the epithelial tissue, and using reverse iontophoresis to at least partially cause an advective flow of the biofluid from the epithelial tissue into the device; and
   a collector for transporting the biofluid from the epithelial tissue into the device.

2. The device of claim 1, further comprising:
   an analyte-specific sensor for sensing the analyte in the biofluid.

3. The device of claim 2, wherein said analyte-specific sensor is adapted to continuously sense the analyte.

4. The device of claim 2, further comprising:
   a coupler configured to transport the biofluid from the collector to the analyte-specific sensor.

5. The device of claim 1, wherein said epithelial tissue is an epidermis and the advective flow is driven by reverse iontophoresis.

6. The device of claim 1, wherein said epithelial tissue is a sweat gland epithelium and the advective flow is partially driven by sweat generation in sweat glands.

7. The device of claim 1, wherein said epithelial tissue is an oral mucosa and the advective flow is driven by reverse iontophoresis.

8. The device of claim 1, wherein said epithelial tissue is a saliva gland epithelium and the advective flow is driven by saliva generation in salivary glands.

9. The device of claim 1, wherein said device is adapted to topically deliver the agent.

10. The device of claim 1, further comprising:
a reservoir containing the agent, the agent in the reservoir being in electrical contact with the iontophoresis electrode.

11. The device of claim 1, further comprising:
a membrane separating the agent and the epithelial tissue, wherein said membrane limits diffusion of the agent unless iontophoresis is applied.

12. The device of claim 1, wherein said agent is selected from the group consisting of: a chelator, a lipid, and a protein.

13. The device of claim 1, wherein said agent is selected from the group consisting of a polycarboxylate and a polycarboxylic acid.

14. The device of claim 1, wherein said agent is selected from the group consisting of ethylenediaminetetraacetic acid, citric acid, and a conjugate base thereof.

15. The device of claim 1, wherein said agent is selected from the group consisting of: oleic acid, caprylic acid, lysophosphatidic acid, and *Zonula occludens* toxin.

* * * * *